United States Patent [19]

Rantala

[11] Patent Number: 5,111,827
[45] Date of Patent: May 12, 1992

[54] RESPIRATORY SAMPLING DEVICE

[75] Inventor: Börje Rantala, Helsinki, Finland

[73] Assignee: Instrumentarium Corp., Finland

[21] Appl. No.: 633,979

[22] Filed: Dec. 26, 1990

Related U.S. Application Data

[63] Continuation-in-part of Ser. No. 292,933, Jan. 3, 1989, abandoned.

[30] Foreign Application Priority Data

Feb. 11, 1988 [FI] Finland .................. 880624

[51] Int. Cl.⁵ .......................... A61B 5/08; A61B 5/087
[52] U.S. Cl. .................... 128/719; 128/725;
73/861.04; 73/861.42; 73/861.65; 73/23.2;
73/23.3
[58] Field of Search .......... 128/716, 718–720,
128/725, 726, 730; 73/861.04, 861.42, 861.65,
23

[56] References Cited

U.S. PATENT DOCUMENTS

| | | | |
|---|---|---|---|
| 3,924,612 | 12/1975 | Dempster et al. | 128/725 |
| 4,034,743 | 7/1977 | Greenwood et al. | 128/725 |
| 4,368,740 | 1/1983 | Binder | 128/719 |
| 4,413,632 | 11/1983 | Schlessinger et al. | 128/716 |
| 4,558,710 | 12/1985 | Eichler | 128/720 |
| 4,581,942 | 4/1986 | Ogura et al. | 128/719 |
| 4,608,995 | 9/1986 | Linnarsson et al. | 128/719 |
| 4,619,269 | 10/1986 | Cutler et al. | 128/719 |
| 4,793,357 | 12/1988 | Lindstrom | 128/719 |
| 4,809,706 | 3/1989 | Watson et al. | 128/725 |
| 4,815,459 | 3/1989 | Beran | 128/719 |
| 5,022,406 | 6/1991 | Tomlinson | 128/725 |

Primary Examiner—Lee S. Cohen
Assistant Examiner—Krista M. Pfaffle
Attorney, Agent, or Firm—Andrus, Sceales, Starke & Sawall

[57] ABSTRACT

An intubation tube contains both a sampling connector (2) for a gas analyzer and a spirometer (18). Spirometer (18) and sampling connector (2) are manufactured so that, in operation, they make up a single unit which is linked via outflow tubes 6 and 7 to pressure and/or flow measuring elements (12, 13) as well as via a sampling tube (9) to a gas analyzer (10). A microprocessor adjusts the flow rate in accordance with the composition of the gas as determined by the gas analyzer.

6 Claims, 3 Drawing Sheets

RESPIRATORY SAMPLING DEVICE

This application is a continuation-in-part of application Ser. No. 07/292,933 filed Jan. 3, 1989abandoned.

The present invention relates to a spirometer connectable to an intubation tube and a sampling connector for a gas analyzer as well as an application of the sampling connector.

BACKGROUND OF THE INVENTION

In anaesthesia, with the patient connected to a respirator, it is often desirable to monitor the alveolar gases of a patient for their composition and pressure as well as flow and volume quantities.

The flow and volume quantities are often monitored through use of a spirometer which is connectable to an intubation tube. One common type of spirometer is a so-called pneumotachometer which provides a slight constriction in the flow path, whereby the flow rate can be calculated on the basis of a pressure difference created thereover. However, the measurement is rather inaccurate for several reasons, the most significant of which is the dependence of the pressure difference on the viscosity of a gas, i.e., actually on the composition of a gas. The pneumotachometer can be fitted in a patient tubing as a disposable product, which aids in eliminating sterility problems. Otherwise, the pneumotachmeter would be quite an attractive flow sensor thanks to its simplicity.

The composition of gases is often determined by directing a flow sample from the mouth of a patient into a gas analyzer.

SUMMARY OF THE INVENTION

An object of the invention is to provide a sampling connector which is capable of eliminating the above drawbacks and of decreasing the number of required connectors. In order to achieve this object, the connector of the invention is characterized in that, in actual use, the spirometer and sampling connector make up a single or integral unit which is connected to pressure and/or flow measuring elements as well as via a sampling tube to a gas analyzer.

The application embodiments of the connector of the invention are characterized in that the sampling connector is linked to a gas-analyzing apparatus, said apparatus comprising a gas analyzer, a pressure differential gauge, a pressure gauge and a microprocessor, the microprocessor being adapted for compensating on the basis of the data issued by said gas analyzer, the effect of gas composition on pressure and flow quantities.

DESCRIPTION OF THE DRAWINGS

The invention will now be described with reference made to the accompanying drawings, in which.

DESCRIPTION OF THE ILLUSTRATED EMBODIMENT

Figure 1:
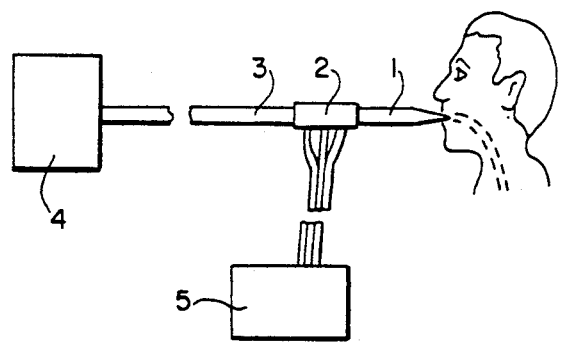
FIG. 1 is a schematic view of a connector of the invention in its operating environment.
Figure 2:
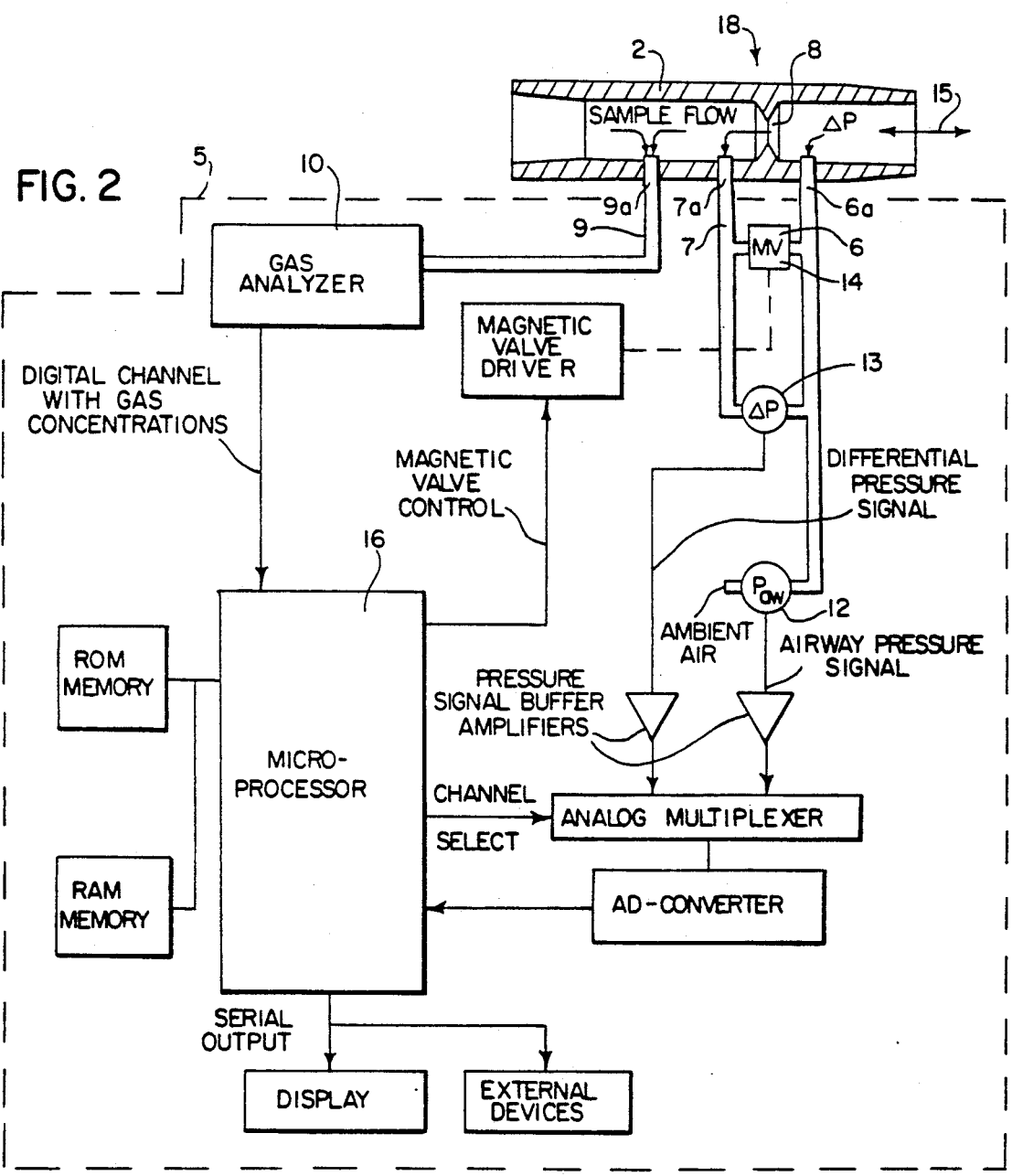
FIG. 2 is a detailed schematic view of the connector shown in FIG. 1 and an analyzing apparatus thereto.

As shown in FIG. 1, a sampling connector 2 is located between an intubation tube or a respiratory tube 1 and a tube 3 leading to a respirator 4, and connector 2 is also connected to an analyzing apparatus 5. As shown in FIG. 2, connector 2 is provided with both a spirometer 18 as well as outflow tubes 6a, 7a and 9a. As shown in FIG. 2, for example, the spirometer can be a pneumotachometer, comprising a restriction or throttle element 8 with outflow tubes 6a and 7a on either side thereof. Outflow tubes 6a and 7a are connected with respective pressure hoses or conduits 6 and 7 to a pressure differential gauge 13 which measures the pressure differential across restriction 8 and issues measuring data for determining the flow rate and further the volume flow. For measuring the respiratory tract pressure, hose 6 is connected to a pressure gauge 12. The respiratory tract pressure or airway pressure is the direct pressure difference between the airway tube 6 and ambient air without further corrections other than conventional zero set and scaling.

Figure 4:
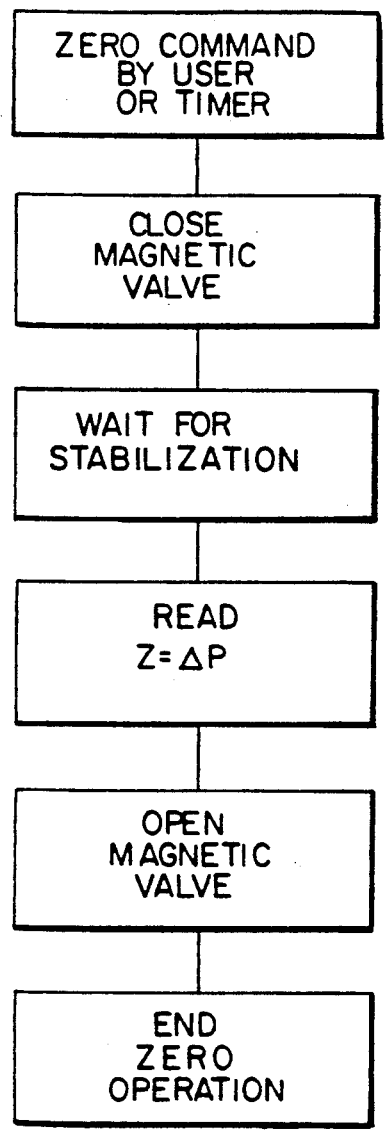
FIG. 4 is a block diagram showing the manner of zeroing the pressure differential gauge.
Figure 5:
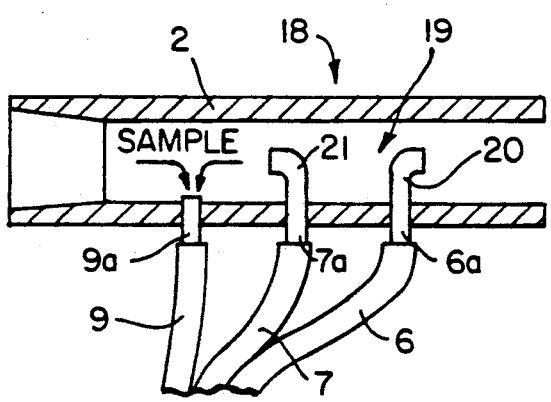
FIG. 5 shows a second embodiment of the connector of the invention.

For zeroing said pressure differential gauge 13, the analyzing apparatus 5 is fitted with a magnetic valve 14, the opening of which short-circuits pressure differential gauge 13, i.e., connects hoses 6 and 7 directly to each other. The manner of zeroing of the pressure differential gauge 13 is shown in FIG. 4. A "zero command" by the user or a timer acts to close the magnetic valve 14. After stabilization, a reading is taken of the pressure differential and the magnetic valve is then opened to complete the zeroing operation.

Sampling connector 2 is provided with an outflow tube 9a which is connected via a sampling tube or conduit to a gas analyzer 10. Gas analyzer 10 can be provided with a sample pump for producing a sample flow. The gas analyzer 10 is a conventional type and will measure the content of various gases such as carbon dioxide, nitrogen oxide and anesthetic gas.

Figure 3:
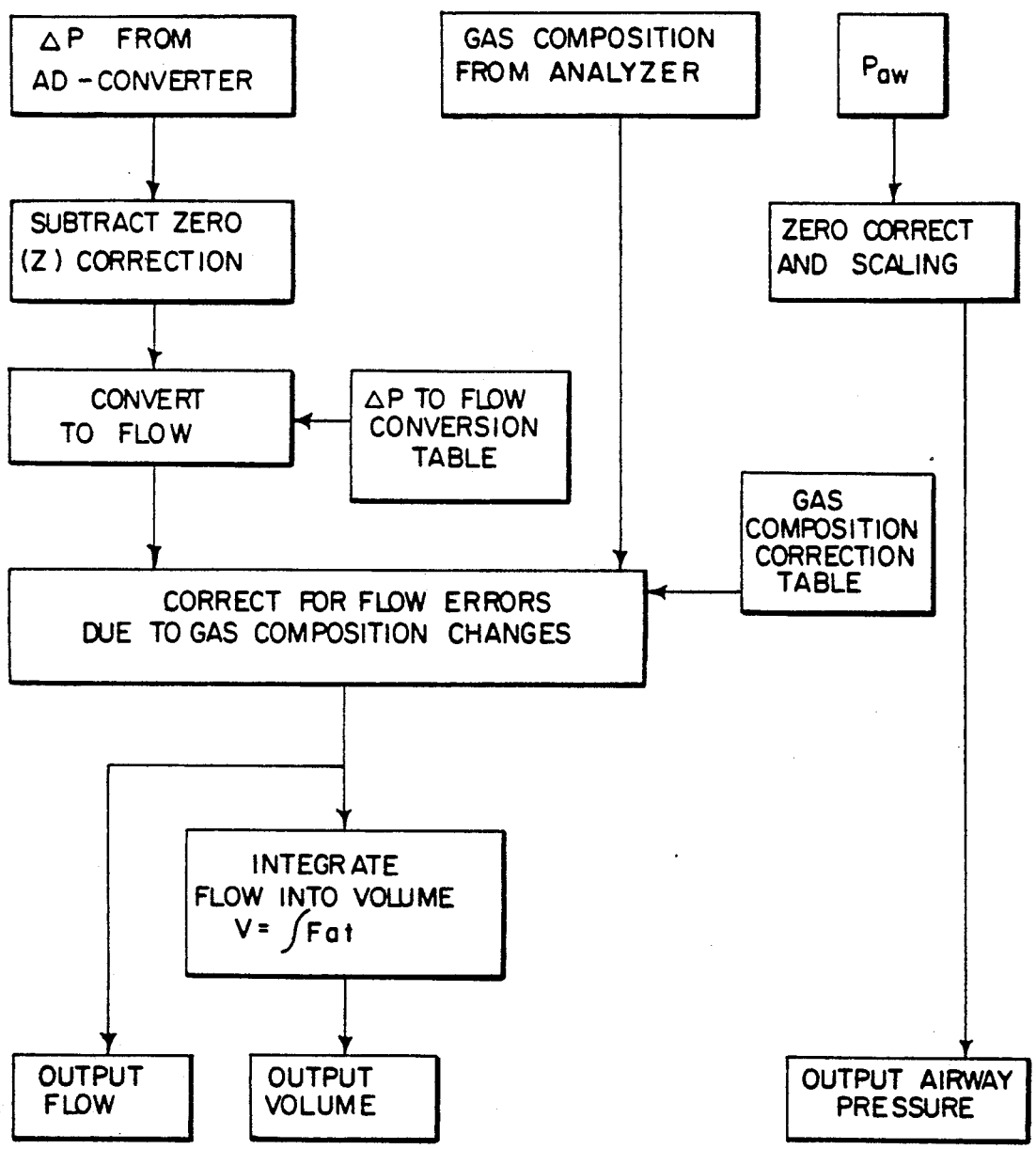
FIG. 3 is a block diagram of the microprocessor program.

Analyzing apparatus 5 is provided with a microprocessor 16 which, on the basis of the data issued by gas analyzer 10, compensates the effect of gas composition on the pressure and flow quantities measured with pressure differential gauge 13, as illustrated in the diagram of FIG. 2. The microprocessor program is shown in the flow chart of FIG. 3.

For measuring a patient flow 15, the spirometer 18 is positioned, relative to outflow tube 9a of gas analyzer 10 of sampling connector 2, on the side towards said intubation tube 1. The sampling connector 2 is suitable for use in measuring both respiratory gases and gases coming out of respirator 4. Typical quantities to be analyzed include the contents of carbon dioxide, nitrogen oxidule and anesthetic gas. Other necessary information includes the pressure of alveolar air and the volume flow of alveolar air.

An advantage gained by a sampling connector of the invention is the fact that it is of simple construction and takes into consideration the effect of condensing water drops and other impurities on the pressure difference flow characteristic curve. In addition, the sampling connector can be injection molded in plastic which provides good dimensional reproducibility in addition to a low price.

The above-described example is only intended for explaining one embodiment of the invention. It is not intended for limiting the scope of protection defined in the annexed claims. FIG. 6 illustrates a modified form of the invention in which a Pitot tube 19 includes a pair of tubes 20 and 21 having open ends that face in opposite directions in connector 2. Tube 20 is connected to conduit 6, while tube 21 is connected to conduit 7. Pitot tube 19 acts in the manner of restriction 8 to provide a measurement of the pressure differential across tubes 20 and 21 and thus an indication of the flow rate.

I claim:

1. A respiratory apparatus comprising a gas intubation tube to conduct a flow of gas, a gas sampling connector mounted in the tube, a spirometer mounted in said tube and spaced longitudinally of said connector, a gas analyzer connected to said sampling connector for measuring the composition of said gas, said spirometer including means for measuring the flow rate of said gas in said tube, and microprocessor means for adjusting the measurement of said flow rate in accordance with the measurement of said composition.

2. The apparatus of claim 1, wherein said flow rate measuring means further comprises a pressure measuring element and a pressure difference measuring element.

3. The apparatus of claim 1, and further comprising first conduit means for connecting the sampling connector with said gas analyzer, said spirometer being disposed between said first conduit means and said intubation tube.

4. The apparatus of claim 1, wherein said spirometer comprises a pneumotachometer.

5. The apparatus of claim 1, wherein said spirometer comprises a Pitot tube.

6. A respiratory apparatus, comprising a gas intubation tube having a first end adapted to be connected to a patient and a second end for connecting to a respirator, gas flow measuring means disposed in said tube for measuring the flow rate of gas passing through said tube, gas analyzing means for measuring the composition of the gas, conduit means for connecting said gas analyzing means and said tube at a location between said gas flow measuring means and said respirator, and means for adjusting the measurement of the flow rate in accordance with the measurement of the composition of said gas to provide an adjusted flow rate.

* * * * *